United States Patent [19]

Segawa et al.

[11] 4,066,413
[45] Jan. 3, 1978

[54] GAS COMPONENT DETECTION APPARATUS

[75] Inventors: Yoshihiro Segawa; Susumu Sato; Eturo Yasuda; Tadashi Hattori, all of Okazaki; Keiji Aoki, Susono, all of Japan

[73] Assignees: Nippon Soken, Inc., Nishio; Toyota Jidosha Kogyo Kabushiki Kaisha, Toyota, both of Japan

[21] Appl. No.: 662,956

[22] Filed: Mar. 1, 1976

[30] Foreign Application Priority Data

Mar. 3, 1975 Japan .................................. 50-26374
Dec. 15, 1975 Japan .................................. 50-149729

[51] Int. Cl.² .......................................... G01N 27/16
[52] U.S. Cl. ................................................. 23/254 E
[58] Field of Search ............. 23/254 E, 255 E, 232 E; 73/27 R; 340/237 R

[56] References Cited

U.S. PATENT DOCUMENTS

| | | | |
|---|---|---|---|
| 2,762,568 | 9/1956 | Sullivan | 23/254E |
| 3,242,717 | 3/1966 | Matle et al. | 23/254 E X |
| 3,251,654 | 5/1966 | Palmer | 23/254 E X |
| 3,479,257 | 11/1969 | Shaver | 340/237 R |
| 3,676,820 | 7/1972 | Taguchi | 23/254 E X |
| 3,865,550 | 2/1975 | Bott et al. | 23/232 E |
| 3,901,067 | 8/1975 | Boardman, Jr. et al. | 23/254 E X |
| 3,932,246 | 1/1976 | Stadler | 23/254 E X |

Primary Examiner—Robert M. Reese
Attorney, Agent, or Firm—Cushman, Darby & Cushman

[57] ABSTRACT

A gas component detection apparatus for detecting gas components contained in an exhaust gas from a combustion device and determining an air-fuel ratio of an air-fuel mixture supplied thereto. A gas component detecting element composed of a semiconductive metal oxide is contacted by the exhaust gas and exhibits variable electric resistances according to the concentrations of the gas components. The electric resistance is taken out as an electric signal through two electrodes disposed either on the surface of the detecting element exposed to the exhaust gas or within the detecting element adjacent that exposed surface. A porous coating layer having an exhaust gas permeability covers the surface of the detecting element exposed to the exhaust gas so as to prevent poisonous substances contained in the exhaust gas from depositing on that exposed surface of the detecting element. The coating layer is formed of a metal oxide having electrically insulating properties and carries therein a catalyst promoting an oxidation reaction of the exhaust gas. The detecting element exhibits an abruptly changed electric resistance when the actual air-fuel ratio of the air-fuel mixture supplied into the combustion device is deviated from a stoichiometrical air-fuel ratio, thereby enabling the control of the air-fuel ratio of the air-fuel mixture.

21 Claims, 34 Drawing Figures

GAS COMPONENT DETECTION APPARATUS

BACKGROUND OF THE INVENTION

1. FIELD OF THE INVENTION

The present invention relates to a gas component detection apparatus for detecting with high sensitivity and rapid response variations in concentrations of gas components such as oxygen ($O_2$), carbon monoxide (CO) and hydrocarbon (HC) contained in a gaseous mixture. The invention finds its useful application particularly in a gas component detection apparatus for an exhaust gas of an internal combustion engine.

2. DESCRIPTION OF THE PRIOR ART

Gas component detection apparatuses have been widely used in many industrial fields. Lately, as a counter measure to cope with the problem of an exhaust gas of internal combustion engine, the gas component detection apparatuses are employed for determining an air-fuel ratio of an air-fuel mixture supplied to an internal combustion engine.

Heretofore, an electric cell comprising a solid electrolyte such as zirconia has been employed for the detection of the air-fuel ratio of air-fuel mixture supplied to the internal combustion engine. More particularly, the variation in the electromotive force of the cell depending on the concentration of oxygen contained in the exhaust gas was utilized as a measure for indicating a corresponding variation in the air-fuel ratio. Further, it has been also known to employ a semiconductive metal oxide and detect the variation in the electric resistance thereof as a measure to represent the variation in the air-fuel ratio.

In the case of the solid electrolyte cell, the electromotive force is generated by the migration of ions through the lattice defects of the solid electrolyte under thermal excitation, so that when the temperature of the solid electrolyte is lower than 400° C no electromotiveforce is generated. Accordingly, the gas component detection apparatus utilizing such solid electrolyte has a serious drawback such that the response of the apparatus is remarkably lowered when the temperature of the exhaust gas is low as is the case of starting the internal combustion engine.

On the other hand, the detection apparatus utilizing the variation of electric resistance of a semiconductive metal oxide suffers from a disadvantage such that the detection of variation in the air-fuel ratio with respect to a predetermined value can not be effected with a desired accuracy since the characteristic curve representing the resistance variation of the semiconductive metal oxide relative to the variation in the air-fuel ratio has a relatively gentle inclination. Furthermore, when the gas component detection apparatus incorporating the semiconductive metal oxide as the detecting element is employed for determining the air-fuel ratio of the air-fuel mixture supplied to the engine, there arises the following problems. Namely, the surface of the semiconductor detecting element exposed to the exhaust gas during usage of the detection apparatus is deposited and gradually accumulated with poisonous substances such as phosphorus (P), lead (Pb), sulfur (S) and compounds thereof contained in the exhaust gas in addition to $H_2$, CO, HC, $O_2$, whereby the material constituting the detecting element will react with such poisonous substances to form compounds, incurring deterioration of the performance of the semiconductor detecting element. In such case, the characteristic curve of the detecting element is adversely changed. Further, when a catalyst is carried on the surface of the metal oxide constituting the detecting element, the performance or activity of the catalyst is also subjected to deterioration.

SUMMARY OF THE INVENTION

Accordingly, an object of the present invention is to provide a gas component detection apparatus for detecting gas components in an exhaust gas from a combustion device which can operate with high sensitivity and rapid response even when the temperature of the exhaust gas is relatively low.

Another object of the invention is to provide a gas component detection apparatus in which the surface of a gas detecting element of a semiconductive metal oxide adapted to contact the exhaust gas is protected from being directly deposited with poisonous substances contained in the exhaust gas, thereby to stabilize the semiconductive characteristic of the gas component detecting element for a long use life.

A further object of the invention is to provide a gas component detection apparatus in which a catalyst is protected from being degraded in its performance with the poisonous substances contained in the exhaust gas.

In view of the above objects, according to one aspect of the present invention, there is provided a gas component detection apparatus which comprises a gas component detecting element composed of a thin film or a sintered mass of a semiconductive metal oxide, a catalyst composed of catalyst materials such as platinum and disposed on the side of the gas component detecting element exposed to the exhaust gas from a combustion device, and a porous coating layer having an exhaust gas permeability and formed of materials having a heat resistance. The porous coating layer is disposed at the side of the gas component detecting element exposed to the exhaust gas. Further, the detection apparatus is provided with two electrodes disposed either on the surface of the detecting element exposed to the exhaust gas or embedded in the detecting element adjacent that exposed surface in a manner to prevent formation of a short-circuit between the electrodes.

According to another feature of the invention, there is provided a gas component detection apparatus for an exhaust gas from a combustion device such as an internal combustion engine in which the electric resistance of the gas component detecting element of a semiconductive metal oxide is caused to vary abruptly, when the detected air-fuel ratio is deviated from a stoichiometric air-fuel ratio serving as a reference value, thereby to enhance the detection accuracy of the apparatus.

The above and other objects as well as novel features and advantages of the invention will become more apparent from the following description when read in conjunction with the accompany drawings.

DETAILED DESCRIPTION OF PREFERRED EMBODIMENTS

Figure 1A:
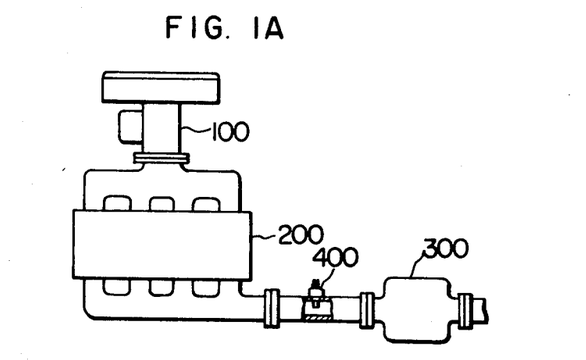
FIG. 1A is a schematic view of an internal combustion engine in which a gas component detection apparatus according to the invention can be employed.
Figure 1B:
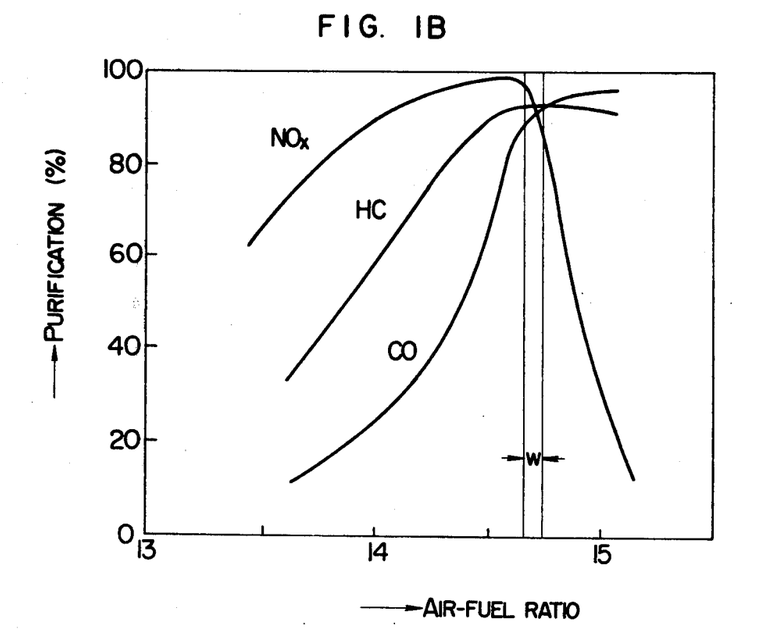
FIG. 1B graphically illustrates a relation between the air-fuel ratio and the purification rate by the catalytic action of a catalyst convertor.

Now, the invention will be described in detail in conjunction with exemplary embodiments thereof. On these embodiments, the gas component detection apparatus according to the invention is intended to be used as a means for determining the air-fuel ratio of the air-fuel mixture supplied to an internal combustion engine. In this connection, reference should first be made to FIG. 1A. The illustrated internal combustion engine 200 having a carbureter 100 is provided with a three-component catalyst converter 300 with a view to eliminating three gas components, that is, CO, HC and NOx. In order to have a catalyst exhibit a maximum performance, it is required to maintain constantly the air-fuel ratio of the air-fuel mixture in a very narrow range W as is shown in FIG. 1B. However, in an ordinary internal combustion engine equipped with a conventional carbureter and fuel injection apparatus, the air-fuel ratio is actually inevitably subjected to a large variation, even when the ratio of an injected fuel to a sucked air is set to become constant. Accordingly, in order to maintain the constant air-fuel ratio, it is necessary to detect the actual air-fuel ratio and feed back the corresponding signal to the carbureter or the injection apparatus; thus controlling the air-fuel ratio of the supplied air-fuel mixture.

To this end, the gas component detection apparatus 400 can be employed. The detection apparatus 400 detects the air-fuel ratio based on the fact that the variation in concentrations of gas components contained in the exhaust gas is closely related to the variation of the air-fuel ratio. In this connection, consideration has to be paid on the fact that the temperature of the exhaust gas as well as the concentrations of the gas components will vary abruptly and remarkably. Therefore, the gas component detection apparatus must be operated with high accuracy for a long use life notwithstanding of such prominent variables. The gas component apparatus according to the invention is constructed to adequately meet this requirement.

Referring to FIGS. 2 to 5, reference numeral 1 denotes a housing of the gas component detection apparatus which is made of a metal material having high electric conductivity and adapted to be mounted on an exhaust manifold or the like portion of the internal combustion engine. To this end, the housing 1 has a threaded portion 1a and a tightening portion 1b. Accomodated at the lower portion within the housing 1 is a disk-like lower holding member 2 which is made of an electrically insulating material such as ceramic and formed with a tapered portion 2a along the lower peripheral edge thereof. As can be seen from FIGS. 2 and 3, the lower holding member 2 is disposed in a counter-bore formed in the lower end portion of the housing 1 and securely held in place with a packing washer 3 interposed between the housing 1 and the top surface of the holding member 2, and a metal ring 4 of high electric conductivity interposed between the tapered portion 2a and the inwardly bent lower end portion of the housing 1 which is formed by heat-caulking. Disposed at the upper portion within the housing 1 is a column-like upper holding member 5 which is also made of an electric insulation material such as ceramic and formed with a tapered portion 5a along the upper edge portion thereof. The upper holding member 5 is fixedly positioned in place by heat-caulking the upper edge portion of the housing 1 with a packing washer 6 and a metal ring 7 interposed between the holding member 5 and the inner wall of the housing 1 in a similar manner as the lower holding member 2. The lower and the upper holding members 2 and 5 are formed, respectively, with paired through-holes 2b, 2c and 5b, 5c extending axially. A first lead wire 8 is inserted into the through-holes 2b and 5b of the lower and the upper holding members 2 and 5. While a second lead wire 9 is inserted through the other holes 2c and 5c of the holding members 2 and 5. These lead wires 8, 9 may be made of a heat-resistant metallic material having a high electric conductivity such as those commercially available under the name of SUS42 or INCONEL 600.

Figure 2:
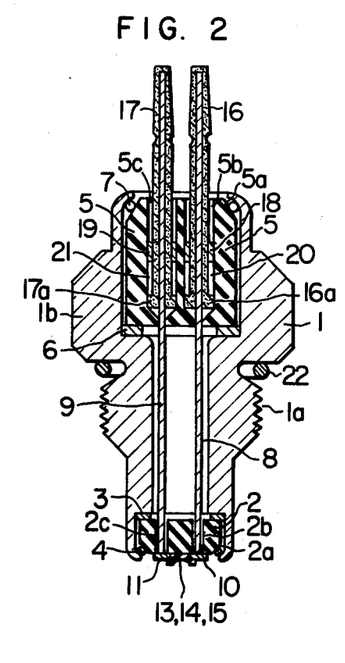
FIG. 2 is a vertical sectional view of a first embodiment of the gas component detection apparatus according to the invention, showing a whole structure thereof.
Figure 3:
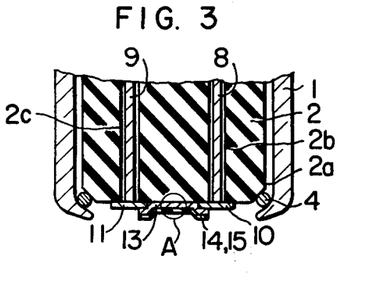
FIG. 3 is an enlarged sectional view showing in detail an arrangement of a gas component detecting element included in the apparatus shown in FIG. 2.
Figure 4:
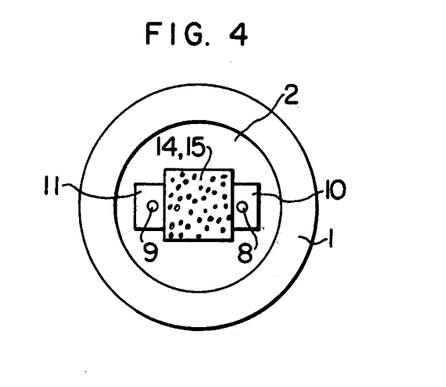
FIG. 4 is a bottom view of the arrangement shown in FIG. 3.

A first thin film electrode 10 is disposed on the underside of the lower holding member 2 in alignment with the through-hole 2b, while a second electrode 11 also in a form of a thin film is mounted in alignment with the other through-hole 2c. These electrodes 10 and 11 may be made of a metal having an excellent heat and corrosion resistance such as gold (Au) and platinum (Pt) and deposited on the lower surface of the holding member 2 by a suitable process such as vacuum evaporation or spattering. The first and the second electrodes 10 and 11 are connected to the associated lead wires 8 and 9, respectively, through an appropriate process such as heat-caulking, plasma welding or the like.

Figure 5:
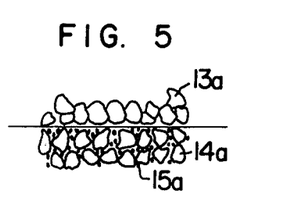
FIG. 5 is an enlarged fragmental view of FIG. 3 showing the portion indicated by A in FIG. 3.

Reference numeral 13 designates a gas component detecting element in a form of a thin film having a thickness preferably in the order of 300 A and formed of a transition metal oxide having a semiconductivity. The gas component detecting element 13 is coated with an insulation layer 14 (FIG. 3) at the lower surface exposed to the exhaust gas. The insulation layer 14 is made of a heat-resisting and porous metal oxide such as γ-alumina ($Al_2O_3$), zirconium dioxide ($ZrO_2$), magnesium oxide (MgO) and has an exhaust gas permeability. It has been found that γ-alumina is most preferable as the metal oxide for the insulation layer 14. In this case, the insulation layer 14 may be conveniently formed through a plasma-injection of γ-$Al_2O_3$ or alternatively by applying a slurry containing γ-$Al_2O_3$ together with a binding agent to the exposed lower surface of the gas component detecting element 13 and thereafter drying and sintering or firing the applied slurry. The insulation layer 14 carries a catalyst 15 composed of catalyst substances such as platinum (Pt), palladium (Pd) and rhodium (Rh). The deposition of the catalyst 15 may be effected through for example a vacuum-evaporation process or a reduction process. In FIG. 5, reference character 13a denotes particles of semiconductive metal oxide constituting the gas component detecting element 13, 14a, designates particles of metal oxide constituting the insulation layer 14 and the symbol 15a denotes particles of the catalyst 15.

The gas component detecting element 13 is disposed at the lower surface of the lower holding member 2 between the first and the second electrodes 10 and 11 and electrically connected to these electrodes.

As the semiconductive metal oxide for the gas component detecting element 13, there may be used titanium oxide (such as $TiO_2$), nickel oxide (NiO), cobalt oxide (CoO), manganese oxide (MnO), zinc oxide (ZnO) and copper oxide (CuO) which are transition metal oxides, as well as tin oxide (such as ($SnO_2$). The detecting element 13 may be formed of suitable one of these semiconductive metal oxides and deposited at the lower surface of the holding member 2 in thickness of 100 A to 10 μ through vacuum evaporation, electron beam evaporation or any other suitable depositing technique.

Referring again to FIG. 2, it can be seen that the through-holes 5b and 5c formed in the upper holding member 5 are enlarged at the upper portions thereof so as to have a larger inner diameter than that of the first and the second lead wires 8 and 9. The annular recesses thus formed between the inner surfaces of the through-holes 5b, 5c and the lead-wires 8, 9 receive a first and a second terminal members 16 and 17 formed with respective collars 16a and 17a at thin lower ends. The collars 16a and 17a, and press-fitted rings 18 and 19 serve to securely hold the terminal members 16 and 17 in place within the respective through-holes 5b and 5c of the upper holding member 5. Further, respective sealing glass materials 20 and 21 are filled in the spaces within the through holes 5b and 5c defined between the collar 16a and the ring 18, and the collar 17a and the ring 19, respectively. The first lead wire 8 is inserted into the first terminal member 16 and welded thereto at the upper end portion, while the second lead wire 9 is inserted into the second terminal member 17 and welded thereto at the upper end portion. Numeral 22 denotes a gasket.

Next, the operation of the gas component detection apparatus of the aforementioned construction will be described. The gas component detection apparatus is mounted on an exhaust manifold of an internal combustion engine through the threaded and the tightening portions 1a, 1b of the housing 1 in such a manner that the gas component detecting element 13 is exposed to the exhaust gas. As is well known, the exhaust gas contains therein gas components such as $O_2$, NOx, CO, HC, $H_2$, $CO_2$ and $N_2$, and the content or concentration of each of these gas components will vary in dependence upon the air-fuel ratio of the air-fuel mixture under unburnt condition. The semiconductive metal oxide constituting the gas component detecting element 13 will be influenced or acted mainly by the concentrations or partial pressures of $O_2$, CO, HC and $H_2$ gases contained in the exhaust gas, and exhibit variable electric resistance values according to the variation in the overall exhaust gas condition brought about by the variation in the partial pressures of these individual gas components.

According to the invention, the insulation layer 14, which is disposed over the surface of the gas component detecting element 13 exposed to the exhaust gas, carries the catalyst 15 serving to enhance the reactivity of the element 13 to the gas components such as $O_2$, CO, HC and $H_2$. In particular, the catalyst 15 increases the sensitivity of the detecting element 13 to the variation in the partial pressure of $O_2$ gas. Therefore, an abrupt and rapid change in the electric resistance value of the detecting element 13 can be produced when the variation in the partial pressure of $O_2$ gas is occurred. This point will be further explained hereunder.

When combustible gas components such as CO, HC and $H_2$ are present along with $O_2$ gas in the vicinity of the surface of the detecting element 13 exposed to the exhaust gas, the following reactions will take place under the action of the catalyst 15.

$$H_2 + \tfrac{1}{2} O_2 \rightarrow H_2O$$

When the air-fuel ratio of the air-fuel mixture is larger under unburnt state than the stoichiometrical air-fuel ratio, some amount of CO, HC and $H_2$ gases will remain unreacted, even after all available $O_2$ gas has been consumed for the reaction with CO, HC and $H_2$. Accordingly, it is estimated that in this case almost no $O_2$ gas will be present in the vicinity of the surface of the gas component detecting element 13. On the other hand, in case where the air-fuel ratio of the air-fuel mixture is smaller before combustion than the stoichiometrical air-fuel ratio, some amount of $O_2$ gas will remain unreacted even after CO, HC and $H_2$ gases have been all reacted with $O_2$ gas. In this case, a certain quantity of $O_2$ gas will exist near the surface of the gas component detecting element 13. It will thus be understood that there are produced near the surface of the detecting element 13 exposed to the exhaust gas two different states of atmosphere; i.e. the state in which a certain quantity of $O_2$ gas is present and the state in which almost no $O_2$ gas exists. Under the action of the catalyst 15 described, the electric resistance value of the gas component detecting element 13 will exhibit an abrupt varietion when the actual or detected air-fuel ratio is changed across the stoichiometrical air-fuel ratio. Thus, a voltage determined by the electric resistance value of the detecting element 13 under the stoichiometrical air-fuel ratio can be used as a reference voltage, with which a voltage determined by the resistance value of the detecting element 13 under the detected air-fuel ratio is to be compared. More particularly, when the latter voltage is larger than the reference voltage, this means that the detected or actual air-fuel ratio is smaller than the stoichiometrical air-fuel ratio and vice-versa. Consequently, it becomes possible to control the actual air-fuel ratio so as to conform it with the stoichiometrical air-fuel ratio.

Figure 6:
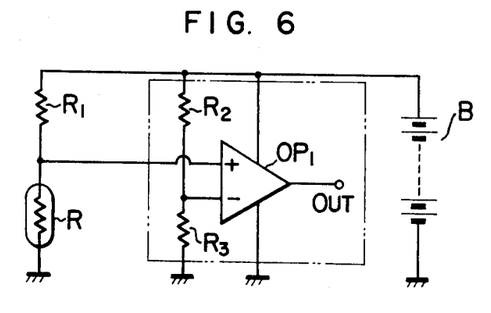
FIG. 6 is a circuit diagram of a control circuit for controlling the air-fuel ratio by utilizing the gas component detection apparatus according to the invention.

FIG. 6 shows an example of an electric circuit which may be used to accomplish the control of the air-fuel ratio. In this circuit, the gas component detecting element 13 is represented by a detector resistor R, and a reference resistor $R_1$ is connected in series to the resistor R. A voltage comparator circuit includes resistors $R_2$ and $R_3$, and a known differential operational amplifier $OP_1$ incorporating integrated circuit. The resistors $R_2$ and $R_3$ serve to set the aforementioned reference voltage. Two input terminals of the operational amplifier $OP_1$ are connected, respectively, to the junction between the detector resistor R and the reference resistor $R_1$ and to the junction between the resistors $R_2$ and $R_3$. The operational amplifier $OP_1$ compares the voltages at the above two junctions and issues at the output terminal an electric signal of logic "1" or "0" level. More particularly, logic "1" signal is produced when the detected air-fuel ratio is smaller than the stoichiometrical air-fuel ratio, and logic "0" signal is produced when the former is larger than the latter.

In this connection, it should be noted that the catalyst 15 carried in the insulation coating or layer 14 covering the surface of the gas component detecting element 13 exposed to the exhaust gas will serve to generate reaction heat upon the reaction of $O_2$ with CO or HC, as a result of which surface temperature of the detecting element 13 is increased. As a consequence, even when the temperature of exhaust gas is low, as at the time of starting the internal combustion engine, the sensitivity of the gas component detecting element 13 will not be reduced.

In the first embodiment described, since the heat-resisting porous insulation coating or layer 14 having exhaust gas permeability covers the surface of the gas component detecting element 13 exposed to the exhaust gas, the poisonous substances such as P, Pb and S contained in the exhaust gas will scarcely adhere directly to that surface of the element 13. Accordingly, there will scarcely happen the case where the poisonous substances react with the semiconductive metal oxide constituting the detecting element 13 and thereby forming compounds. Thus, the characteristic of the detecting element 13 as a semiconductor can be maintained stable for a long period. Further, since the insulation layer 14 is porous and thus has the exhaust gas permeability, the exhaust gas can adequately contact the detecting element 13. In this connection, it should be noted that the catalyst 15 is carried and diffused in the porous insulation layer 14, so that the total active area of the catalyst 15 is fairy increased. Consequently, the oxidation reactions among the gas components are accelerated, and thus the sensitivity of the gas component detecting element 13 to the variation in the concentrations of the gas components is extremely improved. The insulation layer 14 is effective also to protect the catalyst 15 from being deteriorated due to the action of the poisonous substances described above.

Figure 7:
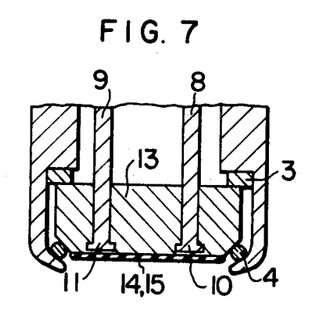
FIG. 7 is a sectional view showing in detail an arrangement of the gas component detecting element in a second embodiment of the invention.

FIG. 7 shows a second embodiment of the present invention, in which the detecting element 13 is constituted by a disk-like body composed of a sintered semiconductive metal oxide such as $TiO_2$. The disk-like detecting element 13 has a diameter of about 8 mm and a thickness of about 4 mm. The first and the second electrodes 10 and 11 are disposed within the detecting element 13 adjacent the surface thereof over which the insulation layer 14 is applied. The insulation layer 14 carries the catalyst 15 consisting of the catalyst substances such as Pt.

Figure 8:
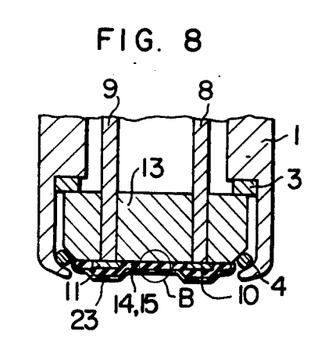
FIG. 8 is a similar view to FIG. 7 showing a construction of the gas component detecting element of a third embodiment of the invention.
Figure 9:
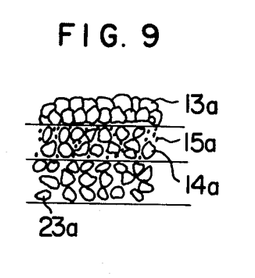
FIG. 9 is a fragmental enlarged view of a portion indicated by B in FIG. 8.

FIGS. 8 and 9 show a third embodiment of the present invention. As is the case of the second embodiment, the gas component detecting element 13 of the third embodiment is composed of a sintered semiconductive metal oxide such as $TiO_2$. The surface of the detecting element 13 exposed to the exhaust gas is coated and covered with the porous insulation layer 14 made of heat-resisting materials such as $\gamma\text{-}Al_2O_3$ and has the exhaust gas permeability. The first and the second electrodes 10 and 11 are disposed on the surface of the detecting element 13 over which the insulation layer 14 is coated. As do the first and the second embodiments, the insulation layer 14 carries the catalyst 15 consisting of Pt or the like. Over the surface of the insulation layer 14 exposed to the exhaust gas is coated with an additional insulation layer 23 composed of the same or similar materials as those of the insulation layer 14. In FIG. 9, 23a designates the particles constituting the insulation layer 23.

Figure 10:
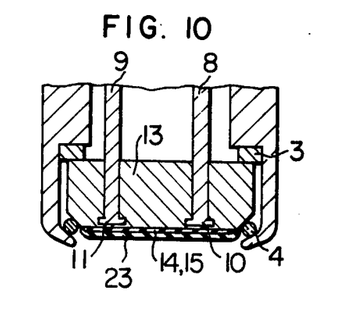
FIG. 10 is a sectional view showing a structure of the gas component detecting element of a fourth embodiment of the invention.

FIG. 10 shows a main portion of a fourth embodiment of the present invention. The fourth embodiment is different from the third embodiment merely in that the first and the second electrodes 10 and 11 are disposed within the detecting element 13 at locations several microns spaced inwards (upward in FIG. 10) from the surface of the detecting element 13 over which the insulation layer 14 is coated.

Figure 11:
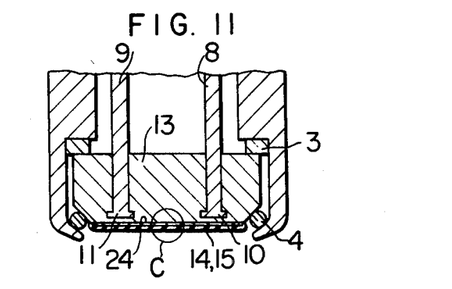
FIG. 11 is a similar view to FIG. 10 showing the gas component detecting element of a fifth embodiment of the invention.
Figure 12:
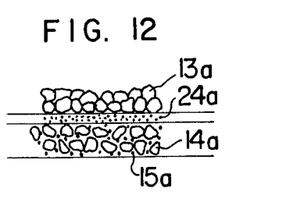
FIG. 12 is a fragmental enlarged view of a portion indicated by C in FIG. 11.

FIGS. 11 and 12 show a main portion of a fifth embodiment of the invention. Also in this embodiment, the gas component detecting element 13 is composed of a sintered semiconductive metal oxide such as $TiO_2$. The electrodes 10 and 11 are disposed within the detecting element 13 at locations several microns inwards from the surface of the detecting element 13 exposed to the exhaust gas. Over the exposed surface of the detecting element 13 is carried a catalyst 24 consisting of catalyst substances such as Pt. The porous insulation layer 14 composed of heat-resisting material such as $\gamma$-$Al_2O_3$ and having the exhaust gas permeability covers the exposed surface of the catalyst 24. As does the previous embodiments, the insulation layer 14 carries the catalyst 15. In FIG. 12, reference character 24a denotes the particles constituting the catalyst 24.

Figure 13:
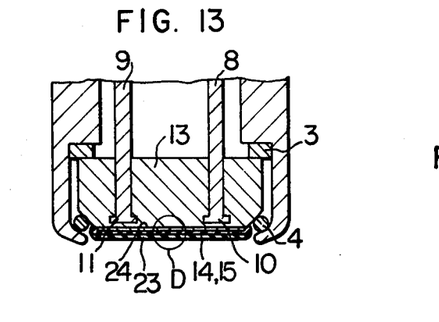
FIG. 13 is a sectional view showing a structure of the gas component detecting element of a sixth embodiment of the invention.
Figure 14:
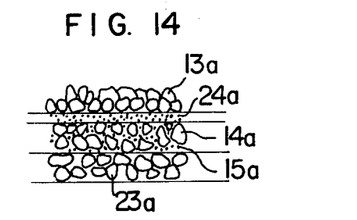
FIG. 14 is a fragmental enlarged view showing a portion designated by D in FIG. 13.

A sixth embodiment shown in FIGS. 13 and 14 is differed from the fifth embodiment shown in FIGS. 11 and 12 in that the surface of the insulation layer 14 exposed to the exhaust gas is coated with an additional insulation layer 23 of the same material as that of the insulation layer 14.

Figure 15:
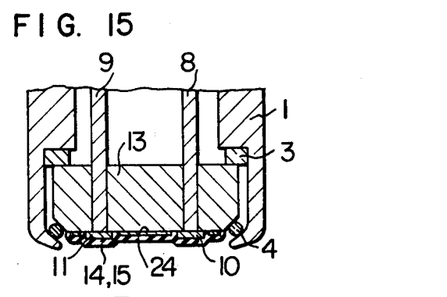
FIG. 15 is a sectional view showing a structure of the gas component detecting element of a seventh embodiment of the invention.

FIG. 15 shows a seventh embodiment of the invention. In this embodiment, the gas component detecting element 13 consists similarly of a sintered mass of transition metal oxides such as $TiO_2$. The first and the second electrodes 10 and 11 are disposed on the surface of the detecting element 13 exposed to the exhaust gas. The catalyst 24 is carried on the latter surface of the detecting element 13 in a manner to prevent formation of a short-circuit between the electrodes 10 and 11. The exposed surface of the catalyst 24 in turn is deposited with a porous insulation layer 14 composed of heat-resisting materials such as $\gamma$-$Al_2O_3$ and having the exhaust gas permeability. The insulation layer 14 carries the catalyst 15.

Figure 16:
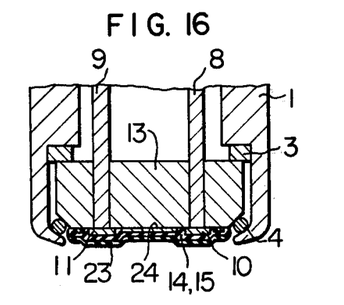
FIG. 16 is a view similar to FIG. 15 and shows a eighth embodiment of the invention.

FIG. 16 shows a main portion of an eighth embodiment of the invention which is different from the seventh embodiment of FIG. 15 in that the exposed surface of the insulation layer 14 carrying the catalyst 15 is coated with another insulation layer 23 of the same material as that of the former.

Figure 17:
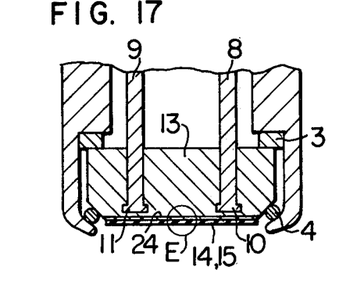
FIG. 17 is a view similar to FIG. 15 and shows a ninth embodiment of the invention.
Figure 18:
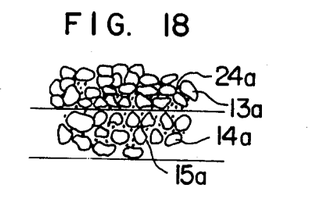
FIG. 18 is a fragmental enlarged view showing a portion designated by E in FIG. 17.

FIGS. 17 and 18 show a ninth embodiment of the invention which is substantially similar in construction to the fifth embodiment shown in FIGS. 11 and 12, except that the catalyst 24 is diffused and carried in the gas component detecting element 13 in the vicinity of the exposed surface thereof. The catalyst 24 is effective to prevent the electrodes 10 and 11 from being short-circuited.

Figure 19:
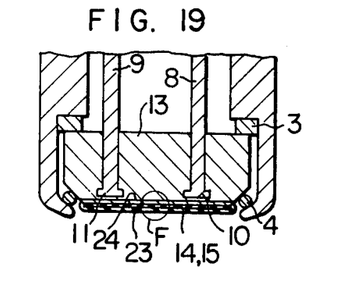
FIG. 19 is a sectional view showing a structure of the gas component detecting element of a tenth embodiment of the invention.
Figure 20:
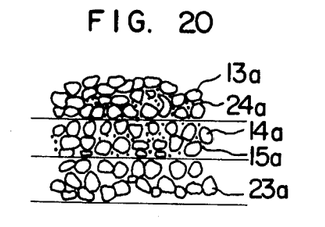
FIG. 20 is a fragmental enlarged view showing a portion designated by F in FIG. 19.

In the tenth embodiment shown in FIGS. 19 and 20, the exposed surface of the insulation layer 14 is coated with another insulation layer 23 of the same material as that of the former.

Figure 21:
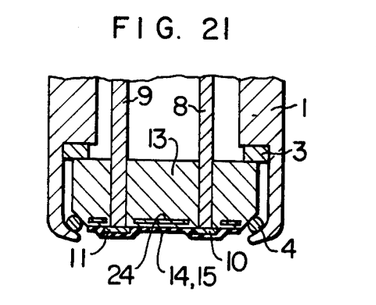
FIG. 21 is a sectional view showing in detail a structure of the gas component detecting element of an eleventh embodiment of the invention.

FIG. 21 shows an eleventh embodiment of the invention which is substantially identical in construction with the seventh embodiment, except that the catalyst 24 is diffused and carried in the gas component detecting element 13 adjacent the exposed surface thereof. Also in this embodiment, the catalyst 24 serves to prevent formation of a short-circuit between the electrodes 10 and 11.

Figure 22:
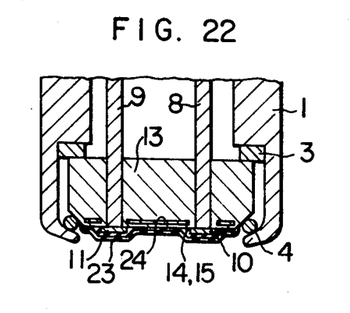
FIG. 22 is a similar view to FIG. 21 and shows a twelfth embodiment of the invention.

FIG. 22 shows a twelfth embodiment which is differed from the eleventh embodiment in that the surface of the insulation layer 14 exposed to the exhaust gas is coated with another insulation layer 23 of the same material.

Figure 23:
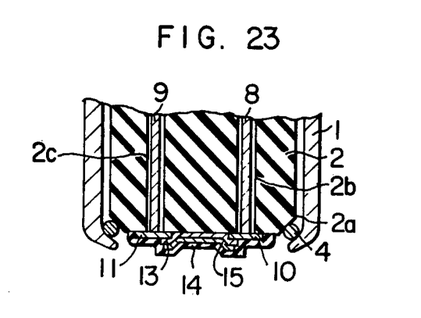
FIG. 23 is a similar view to FIG. 21 and shows a thirteenth embodiment of the invention.

FIG. 23 shows a thirteenth embodiment of the invention. In this embodiment, the gas component detecting element 13 is made of a semiconductive metal oxide such as $TiO_2$ in a form of a thin film. The catalyst 15 is directly carried on the surface of the detecting element 13 exposed to the exhaust gas. The exposed surface of the catalyst 15 is coated with the insulation layer 14 formed of $\gamma$-$Al_2O_3$.

Figure 24:
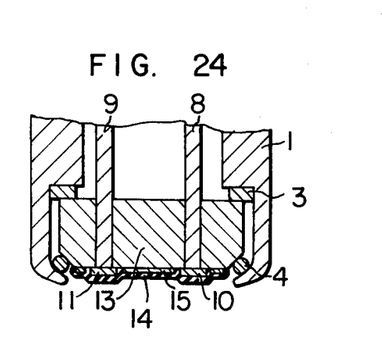
FIG. 24 is a similar view to FIG. 21 and shows a fourteenth embodiment of the invention.

According to a fourteenth embodiment of the invention shown in FIG. 24, the gas component detecting element 13 formed of a sintered mass of semiconductor metal oxides such as $TiO_2$ is directly deposited on its exposed surface with the catalyst 15 so as to prevent formation of a short-circuit between the electrodes 10 and 11. The catalyst 15 is coated with the insulation layer 14 formed of $\gamma$-$Al_2O_3$.

Figure 25:
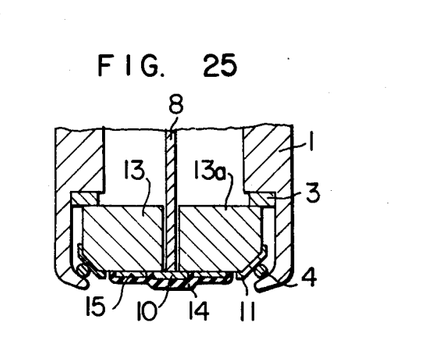
FIG. 25 is also a similar view to FIG. 21 and shows fifteenth embodiment of the invention.

In a fifteenth embodiment of the invention shown in FIG. 25, a sintered mass of $TiO_2$ which is a transition metal oxide is used as the gas component detecting element 13. On the surface of the element 13 exposed to the exhaust gas is disposed the first electrode 10 and the catalyst 15. The electrode 10 and the catalyst 15 are coated with the insulation layer 14. The variation in the electric resistance of the detecting element 13 is take out through the lead wire 8 electrically connected to the first electrode 10 and the housing 1 electrically connected through the metal ring 4 to the second electrode 11 which is attached to the tapered edge portion of the detecting element 13.

Figure 26:
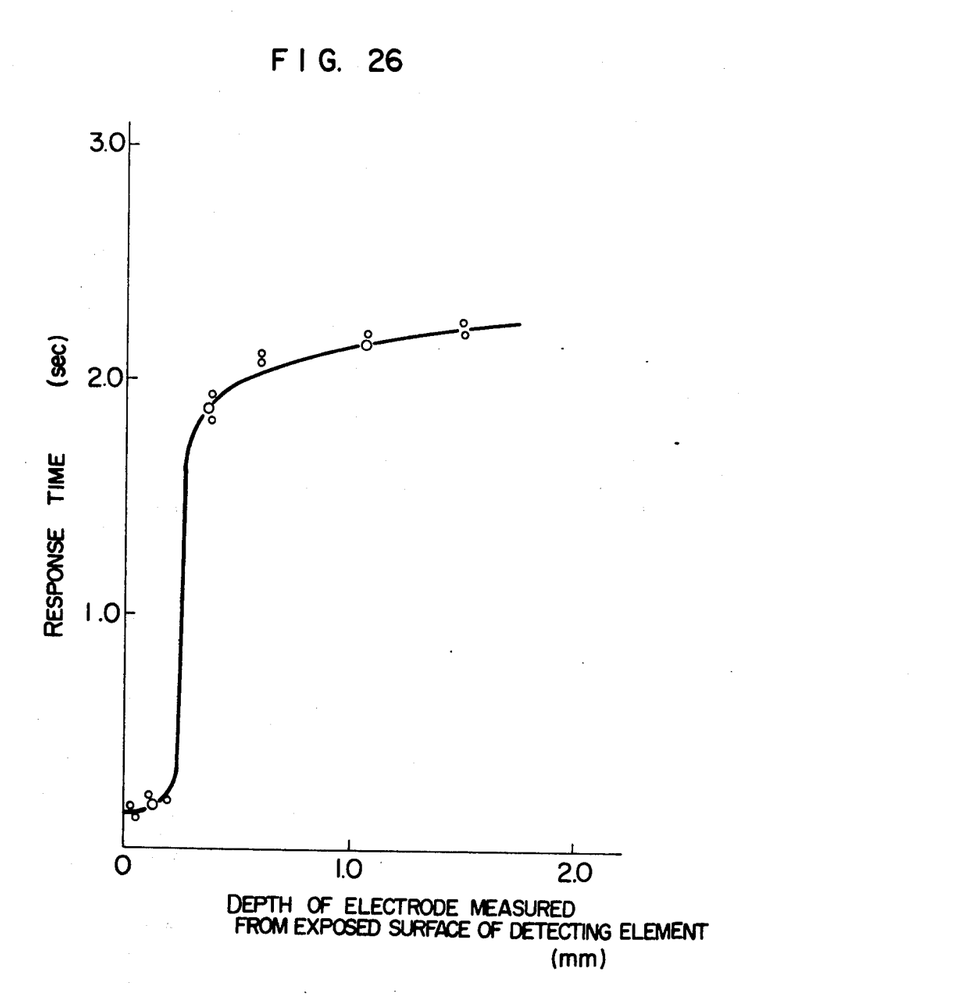
FIG. 26 is a graph to illustrate a relationship between the depth of electrodes as measured from the active surface of a gas component detecting element and a response time of the element.
Figure 27:
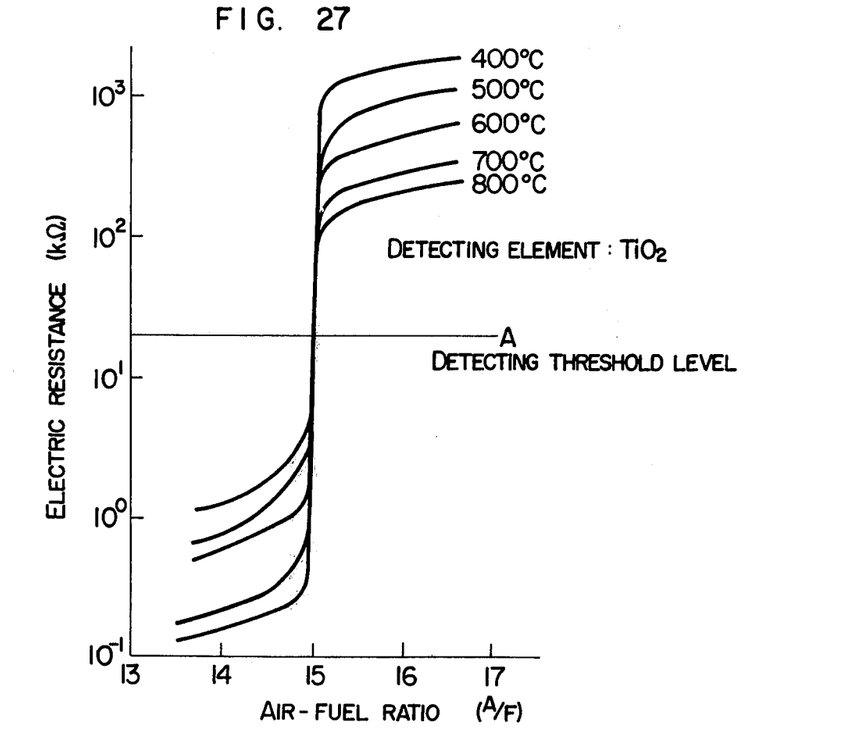
FIGS. 27 to 31 graphically illustrate relation, between the electric resistance variations of the gas component detecting element and the air-fuel ratio in the detection apparatus shown in FIG. 13 in which the gas component detecting element consists of $TiO_2$, $SnO_2$, $Nb_2O_2$ and $NiO$, respectively.
Figure 28:
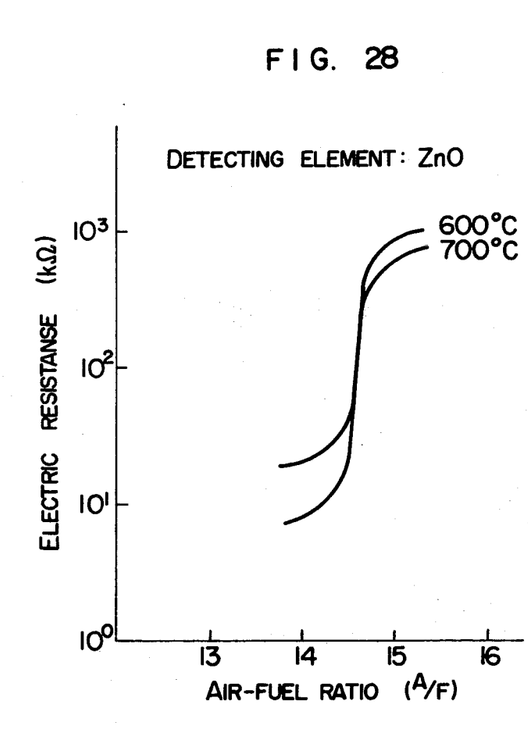
Figure 29:
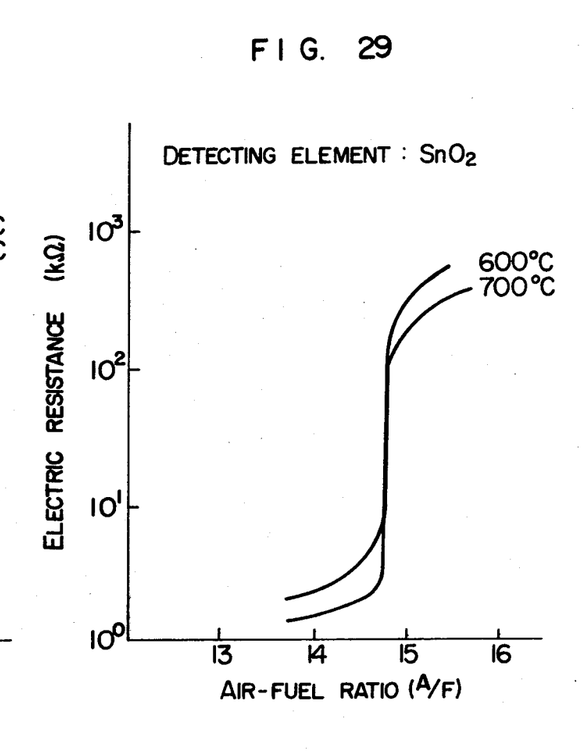
Figure 30:
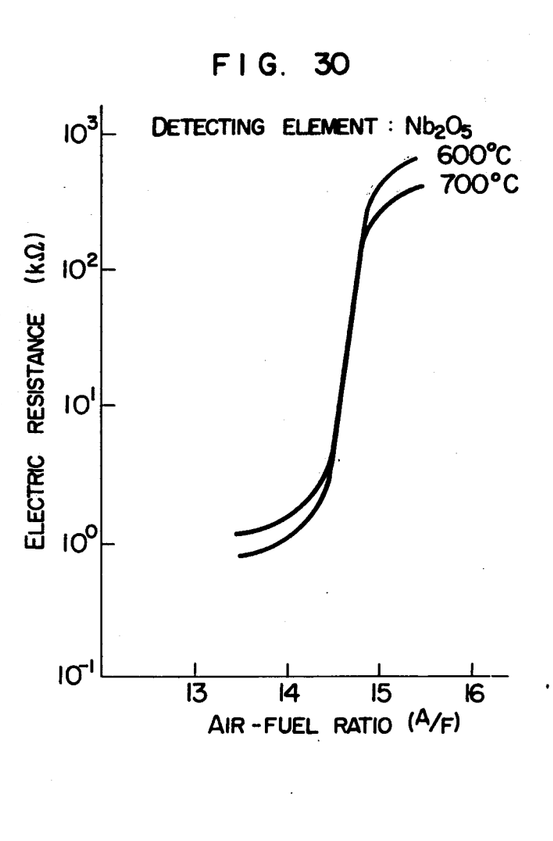
Figure 31:
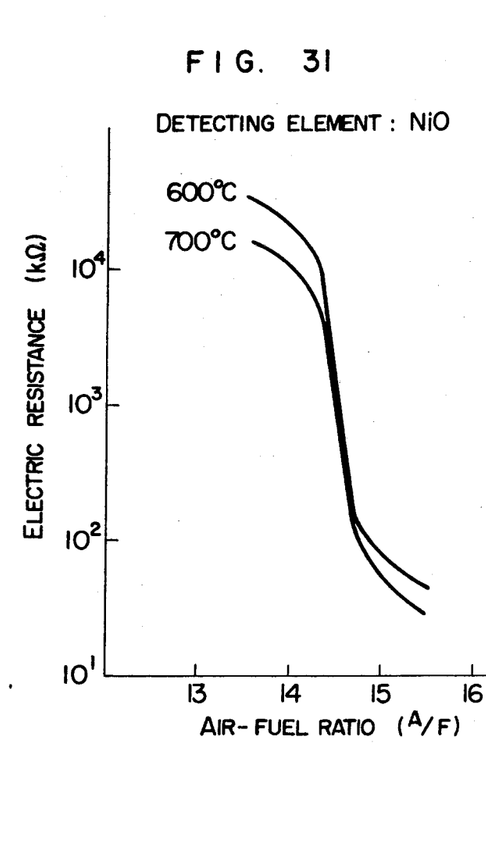

Referring to FIG. 26, there is graphically illustrated a relationship between the response time of change in the electric resistance of the detecting element 13 in response to the variation in the gas component concentration and the positions of the first and the second electrodes 10 and 11. It can be seen from this figure that the response time of the gas component detecting element 13 or the time required for the element 13 changing its resistance value in response to the variation in concentrations of the gas components can be remarkably decreased by positioning the first and the second electrodes 10 and 11 on or adjacent the surface of the detecting element 13 which is to be exposed to the exhaust gas.

In the thirteenth embodiment described hereinbefore, the gas component detecting element 13 has been made of $TiO_2$, $ZnO$, $SnO_2$ and $Nb_2O_3$ (niobium oxide) which are N-type semiconductor materials and $NiO$ a P-type semiconductor material. Then, the characteristics of electric resistances of these detecting elements relative to the air-fuel ratio and the temperature have been measured. The results are graphically illustrated in FIGS. 27 to 31, respectively. It can been seen from these graphs that the electric resistance of the detecting element will change rapidly in the vicinity of the stoichiometrical air-fuel ratio and that the electric resistance is not subjected to the influence of the temperature of the exhaust gas in the region near the stoichiometrical air-fuel ratio. In these graphs, the electric resistance (K $\Omega$) of the gas component detecting element 13 is taken along the ordinate in a logarithm scale, while the air-fuel ratio (A/F) is taken along the abscissa in equalized division.

It will be understood from the above fact that the compensation for the exhaust gas temperature will be unnecessary if the detection threshold level is set with high accuracy. Thus, the gas component detection apparatus according to the invention can be advantageously utilized for the control of the air-fuel ratio in the internal combustion engine of motor cars in which the temperature of the exhaust gas undergoes large variation in dependence upon the operating or running conditions.

It is also noticed that the detection of the air-fuel ratio can be effected without appreciable errors since the electric resistance varies abruptly in the neighborhood of the stoichiometrical air-fuel ratio.

It is further to be noted that, in the case of the fifth, seventh, ninth and eleventh embodiments of the gas component detecting apparatus according to the invention in which the catalyst 24 is deposited on the surface of the gas component detecting element 13 or diffused therein adjacent that surface in addition to the catalyst 15 carried by the insulation layer 14, the sensitivity of the detecting element 13 to the variation in concentrations of gas components can be protected from being lowered by virtue of the presence of catalyst 24, even if the catalyst 15 carried by the insulation layer 14 is degraded due to the action of poisonous substances contained in the exhaust gas.

On the other hand, in the case of the third, fourth, sixth, eighth, tenth and twelfth embodiments of the invention in which the insulation layer 14 carrying the catalyst 15 is coated with the additional insulation layer 23, a large part of poisonous substances contained in the exhaust gas is caught by the outermost insulation layer 23 and the remaining part of the poisonous substances escaped from the insulation layer 23 is then caught by the inner insulation layer 14. Thus, the poisonous substances are effectively prevented from being deposited or accumulated on the surface of the detecting element 13. This feature also contributes to the prevention of deterioration of the catalyst 15.

With a view to clarify the advantageousnesses of the detection apparatus according to the invention over the hitherto known detecting apparatuses, durability tests have been conducted to show how the characteristic of resistance variation in response to the variation in the air-fuel ratio as well as the response time of the detecting element to the variation in the concentration of gas components are changed after use of the detection apparatus for a long period. On the test, the detection apparatus according to the first, third, seventh and the eighth embodiments of the invention have been used along with two conventional detecting apparatuses having no insulation layer, one of which has catalyst carried directly on the surface of the detecting element exposed to the exhaust gas, while the other has no catalyst.

The measuring conditions and the durability test conditions are summarized as follows;

(1) Measuring conditions:
 Four-cylinder engine of 2000 (c.c.) capacity
 (having fuel injection apparatus)
 Engine speed: 2000 r.p.m.
 Negative pressure in the intake manifold: −240 mmHg
 Temperature of exhaust gas: 590° C
 Gasoline used: lead-free gasoline (lead content: 0.02 g/gallon)
(2) Durability test conditions:
 Duration: 100 hours
 Four-cylinder, 1600 (c.c.) engine (with a carburetor)
 Engine speed: 3000 r.p.m.
 Negative pressure in the intake manifold: −240 mmHg
 Gasoline used: lead-free gasoline (lead content: 0.02 g/gallon)

The materials or substances of the gas component detecting portions according to the first, third, seventh and the eighth embodiments of the invention as well as the prior detectors are listed up in the following Table 1.

Table 1

| Examples | Lead Wires (8, 9) | Electrodes (10, 11) | Detecting Element (13) | Insulation Layer (14) | Catalyst (15) | Insulation Layer (23) | Catalyst (24) |
|---|---|---|---|---|---|---|---|
| Embodiment 1 | Pt (0.5 φ) | Pt | TiO$_2$ | γ-Al$_2$O$_3$ (2 mm thick) | Pt | None | None |
| Embodiment 3 | Same | Same | Same | Same | Same | γ-Al$_2$O$_2$ (0.2 mm thick) | None |
| Embodiment 7 | Same | Same | Same | Same | Same | None | Pt |
| Embodiment 8 | Same | Same | Same | Same | Same | γ-Al$_2$O$_3$ (0.2 mm thick) | Same |
| Prior Art 1 | Same | Same | Same | None | Same | None | None |
| Prior Art 2 | Same | Same | Same | None | None | None | None |

The insulation layers 14 and 23 have been formed by applying slurries of γ-Al$_2$O$_3$ and thereafter firing the same; and the catalysts 15 and 24 have been deposited on the gas component detecting element 13 by immersing the element 13 in the solution of H$_2$PtCl$_4$.6H$_2$O, reducing with hydrogen and finally firing it.

Figure 32:
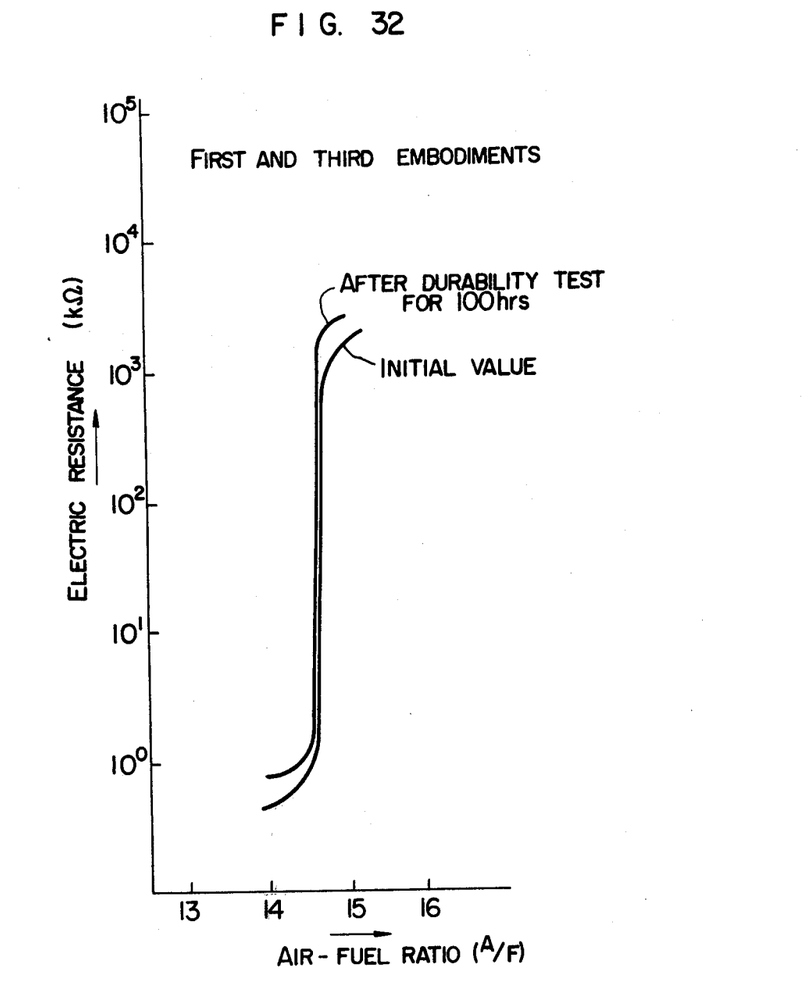
FIGS. 32 and 33 graphically illustrate changes in the relation between the electric resistance of the gas component detecting element and the air-fuel ratio before and after the durability test.
Figure 33:
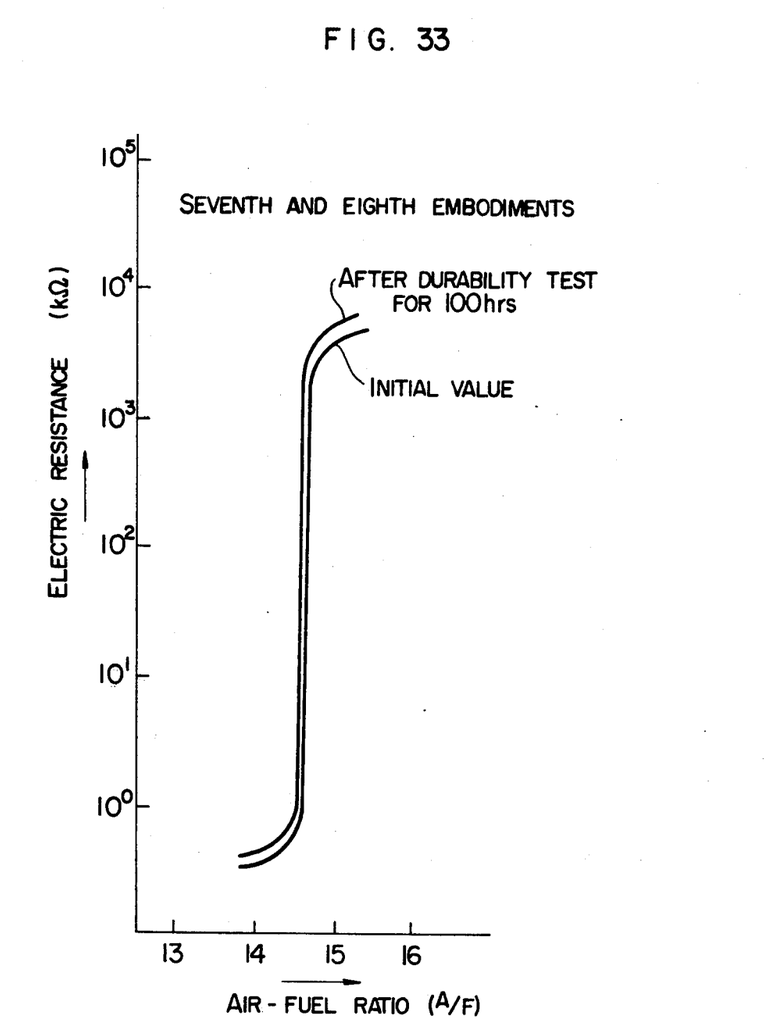

The change in the response time after the durability test is listed up in Table 2 and the change in the variation characteristic of electric resistances of the detecting apparatuses according to the invention after the durability test is shown in FIGS. 32 and 33.

Table 2

| | Response Times | |
|---|---|---|
| Examples | Initial (new part) | After use (100 hrs.) |
| Embodiment 1 | 200 (m. sec.) | 260 (m. sec.) |
| Embodiment 3 | 230 | 250 |
| Embodiment 7 | 160 | 230 |
| Embodiment 8 | 180 | 200 |
| Prior Art 1 | 140 | 540 |
| Prior Art 2 | 600 | 1000 |

As will be clearly understood from the above Table 2 and the graphs shown in FIGS. 32 and 33, the gas component detection apparatus according to the invention exhibits excellent performances as compared with the hitherto known detection apparatuses. For example, the response times of the conventional detection apparatus after the durability test is remarkably increased, as can be seen from Table 2. This means that the response of the detection apparatus can not immediately follow the variation in the air-fuel ratio in the control thereof. Further, there is an undesirable possibility in the hitherto known detectors that, even when the detected air-fuel ratio has changed from a high value to a low value, the detection apparatus may issue an error signal representing a high air-fuel ratio due to the delayed response of the apparatus. In contrast, in the case of the gas component detection apparatus according to the invention, the response time after the durability test has not been significantly changed from the initial value and remains short as compared with that of the conventional detection apparatus. Further, the variation characteristics of electric resistance of the detecting element remain substantially unchanged after the durability test, as can be seen from FIGS. 32 and 33. The gas component detection apparatus according to the invention is thus immune to the drawbacks of the conventional detection apparatus described above.

Although the results of the durability test for the second, fourth, fifth, sixth, ninth, tenth, eleventh, twelfth, thirteenth, fourteenth and fifteenth embodiments have not been shown herein, it has been found that the detection apparatus according to these embodiments are also far excellent over the hitherto known detection apparatus as exemplified by the prior arts 1 and 2 in the above tables in respect of the performance.

Although the material of the outermost insulation layer 23 of the third, fourth, eighth, tenth and the twelfth embodiments is same as the insulation layer 14, it is of course possible to use a different material. In essence, it is sufficient that the insulation layers or films 14 and 23 are composed of a porous metal oxide having a heat resistivity and an exhaust gas permeability.

Although the invention has been described with reference to the gas component detection apparatus applied to detecting the air-fuel ratio of the air-fuel mixture supplied to the internal combustion engine, it should be appreciated that the invention is never restricted to such application. For example, the invention can be applied to detecting the concentration of gas components (combustion products) exhausted from a combustion apparatus of a blast furnace in order to control the air-fuel ratio of the combustible mixture supplied to the combustion apparatus.

As will be appreciated from the foregoing description, in the gas component detection apparatus according the present invention, the electric resistance of the detecting element varies rapidly and significantly under action of the catalyst when the detected air-fuel ratio is deviated from a certain reference value, i.e. the stoichiometrical air-fuel ratio. Accordingly, it is possible to detect the airfuel ratio with a minimum error and a high accuracy. Further, the detection can be effected without being influenced by temperature of the detected gas. Besides, the temperature of the gas component detecting element can be raised rapidly due to the heat generated by the reaction with the gas component under the action of catalyst, which contributes to an enhancement of response of the detecting element.

When poisonous substances such as P, S, Pb and C are contained in the detected gas, these substances are trapped by the insulation layer(s) without adhering directly to the surface of the gas component detecting element, whereby the possibility of the transition metal oxide of the detecting element reacting with the poisonous substances to form compounds is effectively suppressed. These compounds may possibly involve the deterioration of the semiconductor property of the transition metal oxide. Thus, the performance or the semiconductor property of the gas component detecting element can be maintained in a stabilized condition for a long use life. The porous insulation layer aids to increase the active surface area of the catalyst carried therein thereby to enhance the sensitivity of the gas component detecting element to the variation in the concentrations of gas components contained in the detected gas. The catalyst is also protected from being deteriorated by virtue of the presence of the insulation layer.

According to the invention, the electrodes for sensing the resistance variation of the detecting element is located on the surface of the element coated with the insulation layer or disposed within the element adjacent that surface. Such arrangement assures a rapid response of the detecting element to the concentration variation of the gas components, and allows a detection of the concentration of gas components with high accuracy.

Although the invention has been described with reference to preferred embodiments shown in the drawings, it will be appreciated that the invention is never restricted to them. Those skilled in the art can easily conceive many modifications without departing from the spirit and the scope of the invention.

What is claimed is:

1. A gas component detection apparatus for detecting the concentration of oxygen contained in an exhaust gas from an internal combustion engine and determining an air-fuel ratio of an air-fuel mixture supplied thereto comprising:
   a gas component detecting element composed of a semiconductive metal oxide, said detecting element having a surface and being contacted by an exhaust gas and exhibiting variable electric resistances according to the concentration of oxygen contained therein,
   two electrodes disposed in a spaced relation either on the surface of said detecting element exposed to the exhaust gas or within said detecting element adjacent that exposed surface,
   a catalyst promoting at least an oxidation reaction of the exhaust gas, and
   a porous coating layer having an exhaust gas permeability, said coating layer being formed of a metal oxide having electrically insulating properties,
   said catalyst and said coating layer covering the surface of said detecting element exposed to the exhaust gas.

2. A gas component detection apparatus as defined in claim 1, wherein said detecting element is in the form of a thin film having a thickness of 100 angstoms to 10 microns.

3. A gas component detection apparatus as defined in claim 1, wherein said detecting element is composed of a sintered semiconductive metal oxide.

4. A gas component detection apparatus as defined in claim 1, wherein said coating layer carries said catalyst.

5. A gas component detection apparatus as defined in claim 1, wherein said catalyst is carried on or in the surface of said detecting element exposed to the exhaust gas, and said coating layer covers said catalyst.

6. A gas component detection apparatus as defined in claim 1, wherein one of said electrodes is disposed at a central portion of said detection element and the other at the periphery thereof.

7. A gas component detection apparatus as defined in claim 1, wherein said detecting element is composed of a semiconductive transition metal oxide.

8. A gas component detection apparatus as defined in claim 1, wherein said detecting element is composed of a tin oxide.

9. A gas component detection apparatus as defined in claim 1, wherein said detecting element is composed of a titanium oxide.

10. A gas component detection apparatus as defined in claim 1, wherein said coating layer is formed of γ-alumina.

11. A gas component detection apparatus as defined in claim 1, wherein said catalyst is an electrically conductive metal catalyst and two said electrodes are disposed in positions prevented from forming a short-circuit.

12. A gas component detection apparatus as defined in claim 1, wherein said porous coating layer includes:
   a first layer covering the surface of said detecting element exposed to said exhaust gas and carrying therein said catalyst; and
   a second layer covering said first layer.

13. A gas component detection apparatus as defined in claim 1, wherein said catalyst forms a thin layer interposed between said porous coating layer and the surface of said detecting element exposed to said exhaust gas.

14. A gas component detection apparatus as defined in claim 1, wherein said catalyst is carried in said detecting element in the vicinity of said electrodes.

15. A gas component detection apparatus as defined in claim 1, wherein said electrodes are disposed within said detecting element at locations several microns inward from the surface of said detecting element exposed to said exhaust gas.

16. A gas component detection apparatus as defined in claim 15, wherein a portion of said catalyst forms a catalyst layer interposed between said porous coating layer and the surface of said detecting element exposed to said exhaust gas, and the remaining portion of said catalyst is carried in said porous coating layer.

17. A gas component detecting apparatus as defined in claim 15, wherein a portion of said catalyst is diffused and carried in said detecting element in the vicinity of the surface thereof exposed to said exhaust gas, and the remaining portion of said catalyst is carried in said porous coating layer.

18. A gas component detection apparatus for detecting concentration of oxygen contained in an exhaust gas from an internal combustion engine comprising:
   a detecting element having an outer surface and being composed of a semiconductive metal oxide and exhibiting variable electrical conductivity according to the concentration of oxygen in the exhaust gas from the engine;
   a porous insulation layer coated on the outer surface of said detecting element exposed to the exhaust gas; and
   a catalyst embedded in said insulation layer for promoting at least oxidation of said exhaust gas.

19. A gas component detection apparatus as defined in claim 18, wherein said detecting element is composed of a semiconductive metal oxide selected from the group consisting of titanium oxide, nickel oxide, cobalt oxide, manganese oxide, zinc oxide, copper oxide and tin oxide.

20. A gas component detection apparatus as defined in claim 18, wherein said insulation layer is composed of a material selected from the group consisting of gamma-alumina, zirconium dioxide and magnesium oxide.

21. A gas component detection apparatus as defined in claim 18, wherein said catalyst is composed of a substance selected from the group consisting of platinum, palladium and rhodium.

* * * * *